United States Patent
Yin et al.

(10) Patent No.: US 10,414,746 B2
(45) Date of Patent: Sep. 17, 2019

(54) METHOD AND INTERMEDIATE FOR PREPARING TULATHROMYCIN

(71) Applicant: Zhejiang Hisun Pharmaceutical Co., Ltd., Zhejiang (CN)

(72) Inventors: Mingxing Yin, Zhejiang (CN); Dongdong Wu, Zhejiang (CN); Weijiang Wen, Zhejiang (CN)

(73) Assignee: Zhejiang Hisun Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 16/070,658

(22) PCT Filed: Jan. 18, 2016

(86) PCT No.: PCT/CN2016/071198
§ 371 (c)(1),
(2) Date: Jul. 17, 2018

(87) PCT Pub. No.: WO2017/124222
PCT Pub. Date: Jul. 27, 2017

(65) Prior Publication Data
US 2019/0023681 A1   Jan. 24, 2019

(51) Int. Cl.
| C07D 315/00 | (2006.01) |
| C07H 1/00 | (2006.01) |
| C07H 17/00 | (2006.01) |
| C07H 17/08 | (2006.01) |

(52) U.S. Cl.
CPC ............. *C07D 315/00* (2013.01); *C07H 1/00* (2013.01); *C07H 17/00* (2013.01); *C07H 17/08* (2013.01)

(58) Field of Classification Search
CPC ........ C07D 315/00; C07H 1/00; C07H 17/00; C07H 17/08
See application file for complete search history.

(56) References Cited

U.S. PATENT DOCUMENTS 6,825,327 B2   11/2004   Sklavounos et al.

FOREIGN PATENT DOCUMENTS

| CN | 102260306 A | 11/2011 |
| CN | 102295672 A | 12/2011 |
| CN | 102786569 A | 11/2012 |
| CN | 103641869 A | 3/2014 |

OTHER PUBLICATIONS

International Search Report for Application No. PCT/CN2016/071198 dated Sep. 27, 2016.

*Primary Examiner* — Timothy R Rozof
(74) *Attorney, Agent, or Firm* — Wolf, Greenfield & Sacks, P.C.

(57) ABSTRACT

A method and an intermediate for preparing a tulathromycin. The method includes the following step: in an organic solvent, subjecting a compound represented by formula (II) and an n-propylamine to a ring-opening addition shown below to obtain a tulathromycin represented by formula (I), wherein the organic solvent is a 1,2-propandiol. Tulathromycin obtained using the method has a high purity, with an HPLC purity being 95% and above, and up to 99% and above, satisfying a required purity for preparing a tulathromycin as a pharmaceutical formulation. The method has a high yield, is simple to operate, and is more suitable for industrial production.

20 Claims, No Drawings

METHOD AND INTERMEDIATE FOR PREPARING TULATHROMYCIN

CROSS REFERENCE TO RELATED APPLICATIONS

This Application is a national stage filing under 35 U.S.C. 371 of International Patent Application Serial No. PCT/CN2016/071198, filed Jan. 18, 2016, entitled "METHOD AND INTERMEDIATE FOR PREPARING TULATHROMYCIN", the entire contents of this application is incorporated herein by reference in its entirety.

FIELD

The present disclosure relates to the field of veterinary drug, specifically to a method for preparing tulathromycin and an intermediate thereof.

BACKGROUND

Respiratory tract infection is one of the communicable diseases that are relatively hard to control in animal husbandry, and has serious damage to animal husbandry. When respiratory infections are prevalent, huge economic losses is made to animal husbandry. Thus, how to prevent respiratory infections in livestock such as pigs and cattle is an important research topic for veterinarians and veterinary workers. Since respiratory tract infections are generally multiple infections with numerous pathogenic factors and complicated disease conditions, there is currently no effective prevention method. For animal respiratory infections, while seeking biological control and environmental protection, medical treatment is still the main current approach. The search for an effective, safe, broad-spectrum, high-efficiency and low-residue new antimicrobial agent for respiratory infections is an important direction for the research and development of veterinary drugs.

Tulathromycin, which was developed by Pfizer (U.S.A.), is a macrolide semi-synthetic antibiotic specially for animals, and the chemical structure of which is represented by formula I. Tulathromycin is mainly used for the prevention and treatment of respiratory diseases in pigs and cattle caused by *actinobacillus pleuropneumoniae*, mycoplasma, *pasteurella, haemophilus paracasei* and so on. Especially for the treatment of respiratory system disease of cattle and pigs, there is a very obvious efficacy. Because there are three amino groups in the structure of tulathromycin, it has numerous advantages such as rapid absorption, low dosage, long-lasting efficacy, and single-administration for full-course treatment. Since its launch, it has received extensive attention from the veterinary drug industry at home and abroad.

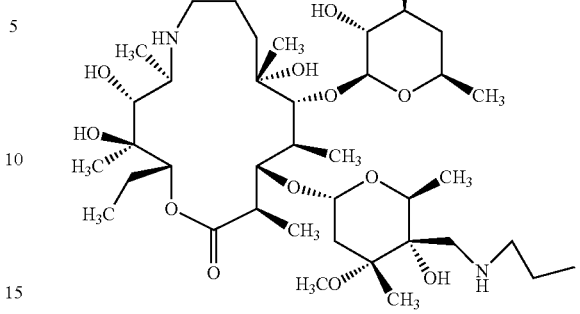

Tulathromycin product-Draxxin is composed of two isomers when it reaches equilibrium in aqueous solution. One is a 15-membered azalides-tulathromycin A (formula I), and the other is a 13-membered azalides-tulathromycin B (Formula I'), and the contents of which are respectively 90% and 10%. Since there is a phenomenon in which two isomers of tulathromycin are balanced in a solution (i.e., a tulathromycin solution, the solute is tulathromycin, and the solvent is selected from the group consisting of water, organic solvent and mixed solvent of water and organic solvent), changes of the solution environment and pH greatly affects the ratio of these two components which imposes higher requirements on preparations. Due to different biological activities of the two isomers, the efficacy of the drug to animals is also affected. Pfizer discloses a method in U.S. Pat. No.6,825,327B2, comprising: in isopropanol solvent, performing a ring-opening reaction by using an epoxidation intermediate and n-propylamine to obtain crude tulathromycin, reacting the crude tulathromycin with phosphoric acid to form a salt, then alkalizing, and recrystallizing to obtain tulathromycin. However, due to the salt formation reaction of crude tulathromycin and phosphoric acid is performed in a mixed solution of organic solvent and water, i.e., there is water in the system of recrystallization process, and due to residue of n-propylamine, the amount of phosphoric acid used is not easy to be precise, and the duration of the recrystallization is long, leading to glycosidic bond cleavage of tulathromycin, resulting in the increase of impurities. In addition, after the subsequent alkalization, the yield and purity of the recrystallized product from dichloromethane/n-heptane system are low, and the impurity removal effect is not obvious. Therefore, there is a need in the art for a method of preparing high-purity tulathromycin.

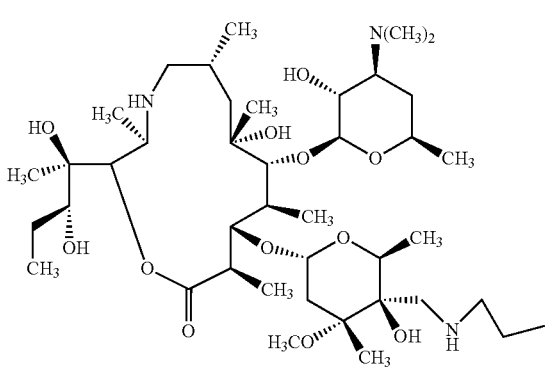

SUMMARY

The technical problem to be solved by the present disclosure is to provide a method for preparing tulathromycin and an intermediate thereof, which aims to overcome the deficiencies of the conventional method for preparing tulathromycin having a low purity, low yield, complicated operations and not suitable for industrial production. Tulathromycin produced by the method of the present disclosure has a high purity which is measured by HPLC as generally more than 95%, and even over 99%, which satisfies the purity requirement of pharmaceutical preparation, and is good for increasing the biological activity and ensuring the treatment efficacy; in addition, the method of the present disclosure has high yield and simple operations, and is more suitable for industrial production.

The present disclosure mainly solves the above technical problems by the following technical solutions.

The present disclosure provides a method for preparing tulathromycin represented by formula I, comprising: subjecting a compound represented by formula II and n-propylamine to ring-opening addition reaction shown below in an organic solvent to produce tulathromycin represented by formula I; wherein the organic solvent is 1,2-propandiol;

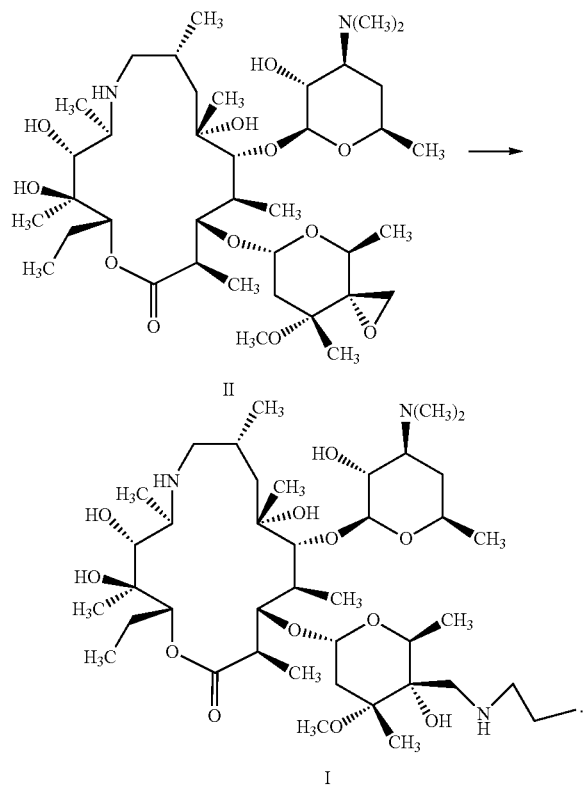

The method for preparing tulathromycin represented by formula I preferably comprises the following steps: mixing a mixed solution of the compound represented by formula II and the organic solvent with n-propylamine, and performing the ring-opening addition reaction.

In the method for preparing tulathromycin represented by formula I, the mole ratio of the compound represented by formula II to n-propylamine can be routine mole ratio of this kind of reactions in the art, preferably from 1:5 to 1:30, and more preferably from 1:8 to 1:15. The amount of the organic solvent is not specifically limited, as long as it does not affect the reaction. The temperature of the ring-opening addition reaction can be routine temperature of this kind of reactions in the art, preferably between 30 and 90° C., more preferably between 40 and 65° C., and most preferably between 45 and 55° C. The course of the ring-opening addition reaction can be monitored by routine detection methods of the art (for example, TLC and/or HPLC), and it is generally detected by HPLC. When the content of the compound represented by formula II is <2%, the reaction is ended. The duration of the ring-opening addition reaction can be routine duration of this kind of reaction in the art, preferably from 15 to 40 hours, and more preferably from 16 to 20 hours.

In a preferred embodiment of the present disclosure, the ring-opening addition reaction is preferably carried out in the condition of gas protection. The gas for the gas protection can be routine gas in the art, preferably nitrogen.

After the ring-opening addition reaction, the method further comprises post-processing treatment. The methods and conditions of the post-processing treatment can be routine methods and conditions of this kind of reaction in the art. In the present disclosure, the post-processing treatment preferably comprises the following steps: removing n-propylamine and the organic solvent after the completion of the ring-opening addition reaction to obtain crude tulathromycin represented by formula I; and performing recrystallization to obtain tulathromycin represented by formula I.

In the post-processing treatment, the method for removing n-propylamine and the organic solvent can be routine methods in the art, preferably concentration under reduced pressure.

In the post-processing treatment, the recrystallization can be routine recrystallization methods for this kind of compound in the art, and the present disclosure preferably comprises the following steps: mixing the crude tulathromycin represented by formula I with a solvent A, then adding an anti-solvent, crystallizing to obtain a product of tulathromycin represented by formula I; wherein, the solvent A is a mixed solvent of acetone and a $C_{1-3}$ alcohol; and the anti-solvent is water or a mixed solvent of water and acetone. In the solvent A, the $C_{1-3}$ alcohol is preferably 1,2-propandiol.

In the recrystallization, the amount of the solvent A is not specifically limited, as long as the crude tulathromycin represented by formula I can be dissolved to obtain clarified and transparent solution. Preferably, the volume to mass ratio of the solvent A to the crude tulathromycin represented by formula I is from 2 mL/g to 50 mL/g, and more preferably from 2 mL/g to 30 mL/g. In the solvent A, the ratio between the amount of acetone and the $C_{1-3}$ alcohol is not specifically limited.

In the recrystallization, the adding of anti-solvent can be routine operation in the art, preferably dropwise adding. The temperature for adding the anti-solvent can be routine temperature in the art, preferably between 35 and 45° C. The amount of the anti-solvent is not specifically limited, as long as tulathromycin represented by formula I can be precipitated; preferably, the volume to mass ratio of the anti-solvent to tulathromycin represented by formula I is from 2 mL/g to 60 mL/g. When the anti-solvent is the mixed solvent of water and acetone, the volume ratio of the water to acetone is preferably from 0.5:1 to 3:1. During adding the anti-solvent in the recrystallization, the adding is finished until the solution A containing tulathromycin represented by formula I turns turbid, the resulting mixture is stirred and crystalline grain culturing is carried out for 10 to 30 minutes, and the remaining anti-solvent is added. The temperature of crystallization can be routine temperature in the art, preferably between 0 and 45° C.

In the recrystallization, the duration of crystallization can be routine duration in the art, preferably from 1 to 6 hours, and more preferably from 1 to 3 hours (for example, 2 hours).

In a preferred embodiment of the present disclosure, during the recrystallization, the crystallization comprises an early stage of crystallization and a late stage of crystallization, wherein, the early stage of crystallization is carried out at a temperature between 35 and 45° C. for 0.5 to 3 hours (for example, 1 hour), and the late stage of crystallization is carried out at a temperature between 0 and 35° C. (for example, between 0 and 10° C.) for 0.5 to 3 hours (for example, 1 hour).

In another preferred embodiment of the present disclosure, during the recrystallization, after the completion of crystallization, filtration, washing and drying are preferably carried out to obtain tulathromycin product represented by formula I.

In another preferred embodiment of the present disclosure, the post-processing treatment preferably comprises the following steps: after the ring-opening addition reaction above, removing n-propylamine, mixing with acetone, adding the anti-solvent, performing crystallization to obtain tulathromycin represented by formula I. Therein, the removing of n-propylamine, amount of acetone, type and amount of the anti-solvent, and crystallization are the same as those above.

The method for preparing tulathromycin represented by formula I preferably further comprises the following method A or method B:

the method A comprises the following steps: with the action of a catalyst and a hydrogen source, subjecting the compound represented by formula III to de-protection reaction shown below in the organic solvent to produce the compound represented by formula II;

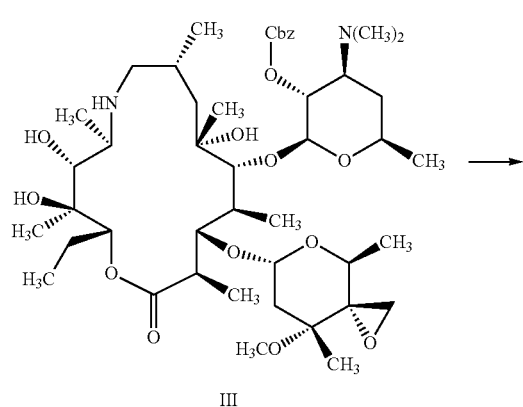

III the method B comprises the following steps: in a mixed solvent of water and a non-polar organic solvent, subjecting the salt IIa of the compound represented by formula II and a base to acid-base neutralization reaction to produce the compound represented by formula II;

wherein in the compound IIa, X is an organic acid or an inorganic acid, and n is 1, 2 or 3.

In method A, the method for preparing the compound represented by formula II preferably comprises the following steps: mixing a mixed solution of the compound represented by formula III and the organic solvent with the hydrogen source and the catalyst, and performing the de-protection reaction.

In method A, in the method for preparing the compound represented by formula II, the organic solvent is preferably a $C_{1-3}$ alcohol and/or a ketone. The $C_{1-3}$ alcohol is preferably selected from the group consisting of methanol, ethanol and isopropanol, or a mixture thereof. The ketone is preferably acetone. The catalyst is preferably palladium-carbon. The mass percentage of palladium in the palladium-carbon is preferably from 3 to 20%, and more preferably form 5 to 15%; the percentage refers to the percentage of the mass of palladium in the total mass of the palladium-carbon. The hydrogen source is preferably ammonium formate. The amount of the catalyst is 5% to 15% of the mass of the compound represented by formula III, and more preferably from 5 to 10%. The amount of the hydrogen source is preferably more than 1 fold of the mole quantity of the compound represented by formula II. The temperature of the de-protection reaction can be routine temperature of this kind of reaction in the art, preferably between 20 and 25° C. The course of the de-protection reaction generally can be monitored by the routine detection method in the art (for example, HPLC). Generally, the reaction is regarded as terminated when the compound represented by formula III disappears. The duration of the de-protection reaction is preferably from 1 to 6 hours, and more preferably from 2 to 3 hours In a preferred embodiment of the present disclosure, in the method A, the de-protection reaction is preferably carried out in the condition of gas protection. The gas for the gas protection can be routine gas of this kind of reaction in the art, preferably nitrogen.

In the method A, after the de-protection reaction, preferably, post-processing treatment is further included. The post-processing treatment can be routine operations of this kind of reactions in the art, preferably including the following steps: subjecting the reaction solution after the de-protection reaction to filtration (diatomite is generally used as a filter-aid), washing ($C_{1-3}$ alcohol is generally used for washing), and removing the solvent (for example, concentration under reduced pressure); mixing with water and organic solvent that is used for extraction (for example, halohydrocarbon solvent, such as dichloromethane), and adjusting the pH to between 9 and 10 with a base (for example, a base selected from the group consisting of potassium carbonate, sodium carbonate, sodium hydroxide and potassium hydroxide, or a mixture thereof); stratifying, and extracting the water layer with the organic solvent being used for extraction (for example, halohydrocarbon, such as dichloromethane); combining the organic layers, washing (for example, washing with saturated salt solution), drying (for example, anhydrous sodium sulfate), and removing the organic solvent.

In method B, the organic acid can be routine organic acid in the art, which is not specially defined, as long as it forms salt with the compound represented by formula II, preferably trifluoroacetic acid. The inorganic acid can be routine inorganic acid in the art, which is not specially defined, as long as it forms salt with the compound represented by formula II. The non-polar organic solvent is preferably halohydrocarbon solvent. The halohydrocarbon solvent is preferably dichloromethane and/or trichloromethane. The base can be routine base in the art, preferably an inorganic base. The inorganic base is preferably selected from the group consisting of potassium carbonate, sodium carbonate, sodium hydroxide and potassium hydroxide, or a mixture thereof. The amount of the mixed solvent is not specifically limited, as long as it does not affect the reaction. The amount of the base is not specifically limited, and the pH of the reaction solution is generally controlled to between 9 and 10. The temperature of the acid-base neutralization reaction can be routine temperature of this kind of reactions in the art. The duration of the acid-base neutralization reaction is preferably 30 minutes.

In method B, after the acid-base neutralization reaction, preferably, post-processing treatment is further included. The post-processing treatment can be routine operations of this kind of reactions in the art, preferably comprising the following steps: after the acid-base neutralization reaction, separating the water layer from the organic layer, and extracting the water layer with a non-polar organic solvent (the non-polar organic solvent is preferably halohydrocarbon solvent); combining the organic layers, washing (for example, washing with saturated salt solution), drying (for example, anhydrous sodium sulfate), filtering, and removing the solvent (for example, concentration under reduced pressure).

In the method A, the method for preparing the compound represented by formula II preferably further comprises the following steps: in the organic solution, with the action of the base, subjecting trimethylsulfonium halide and the compound represented by formula IV to epoxidation reaction shown below to produce the compound represented by formula III;

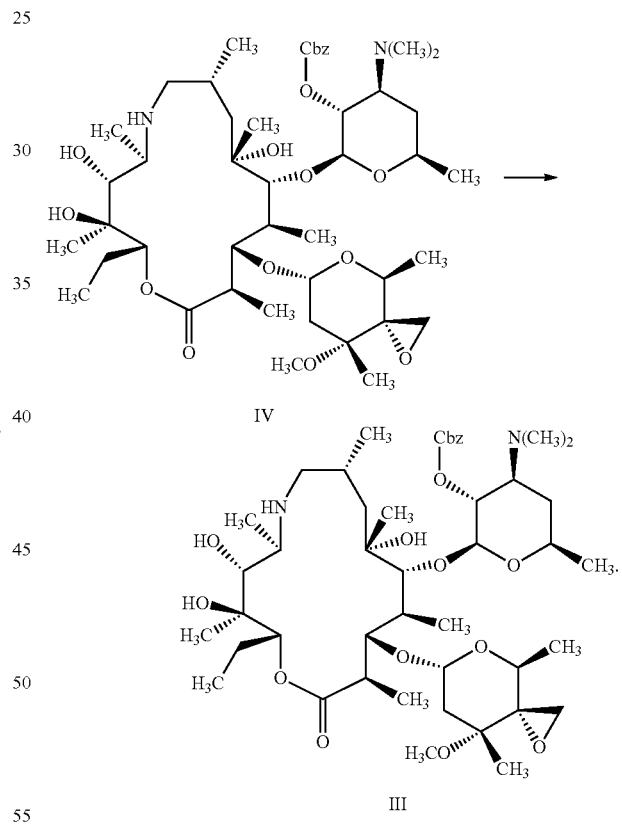

The method for preparing the compound represented by formula III preferably comprises the following steps: mixing the mixed solution of trimethylsulfonium halide and the organic solvent with the base, adding the organic solvent of the compound represented by formula IV and performing the epoxidation reaction.

In the method for preparing the compound represented by formula III, the trimethylsulfonium halide is preferably trimethylsulfonium bromide. The organic solvent is preferably an ether; the ether is preferably tetrahydrofuran (THF). The base is preferably potassium tert-butoxide. The mole ratio of the trimethylsulfonium halide to the compound represented by formula IV is preferably from 2:1 to 10:1, and more preferably from 3:1 to 4:1. The mole ratio of the trimethylsulfonium halide to the base is preferably from 1:1 to 1.2:1. The amount of the organic solvent is not specifically limited, as long as it does not affect the reaction. The temperature of the epoxidation reaction can be routine temperature of this kind of reactions in the art, preferably between −75 and −65° C. The course of the epoxidation reaction is generally monitored by routine detection methods in the art (for example, TLC, HPLC or GC). Generally, the reaction is regarded as terminated when the compound represented by formula IV disappears. The duration of the epoxidation reaction is preferably from 0.5 to 5 hours, and more preferably from 1 to 2 hours.

The temperature for mixing the mixed solution of trimethylsulfonium halide and the organic solvent with the base can be routine temperature in the art, preferably between −15 and −5° C. After mixing the mixed solution of trimethylsulfonium halide and the organic solvent with the base, it is preferably to stir the mixed solution at temperature between −15 and −5° C. for 0.5 to 3 hours (for example, 1 hour). After mixing the mixed solution of trimethylsulfonium halide and the organic solvent with the base, preferably, the temperature of the reaction system is controlled between −75 and −65° C., and an organic solution of the compound represented by formula IV is added. The organic solvent in the organic solution of the compound represented by formula IV is preferably halohydrocarbon solvent. The halohydrocarbon solvent is preferably dichloromethane. In the organic solution of the compound represented by formula IV, the amount of the organic solvent is not specifically limited, as long as the compound represented by formula IV is fully dissolved.

In the method for preparing the compound represented by formula III, the epoxidation reaction is preferably performed under the condition of gas protection. The gas for the gas protection can be routine gas in the art, preferably nitrogen.

After the epoxidation reaction, preferably, post-processing treatment is further included. The post-processing treatment can be routine operations of this kind of reactions in the art, which preferably comprises the following steps: after the completion of the epoxidation reaction, mixing the reaction solution with ammonium chloride aqueous solution to quench the reaction; separating the water layer from the organic layer, and extracting the water layer with the organic solvent (the organic solvent is preferably halohydrocarbon solvent, such as dichloromethane); combining all the organic layers, washing (for example, using saturated salt solution), drying (for example, anhydrous magnesium sulfate and/or anhydrous sodium sulfate), filtering, and removing the solvent (for example, concentration under reduced pressure).

Therein, the method for preparing the compound IV can be routine method in the art. For example, it can be obtained by subjecting the compound represented by formula V to oxidation reaction. The specific reference is made to Example 1 of the present disclosure, or Example 2 of U.S. Pat. No.6,825,327B2. The reaction is shown below:

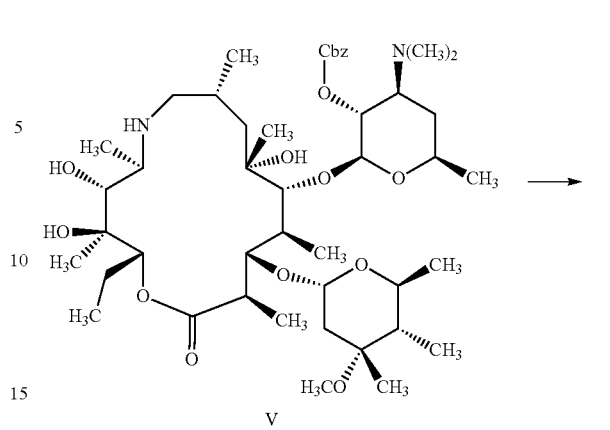

V

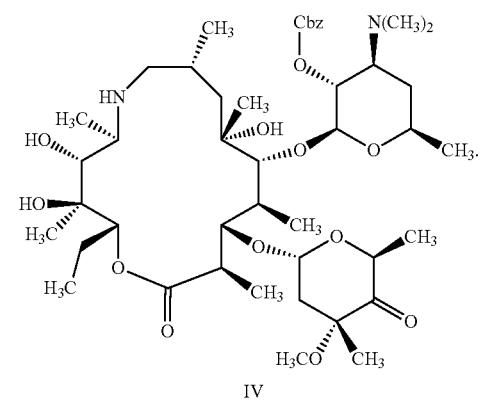

IV

In the method B, the method for preparing the compound represented by formula II further comprises the following steps: in the organic solvent, with the action of the catalyst and the hydrogen source, subjecting the salt IIIa of the compound represented by formula III to the de-protection reaction to produce the salt IIa of the compound represented by formula II;

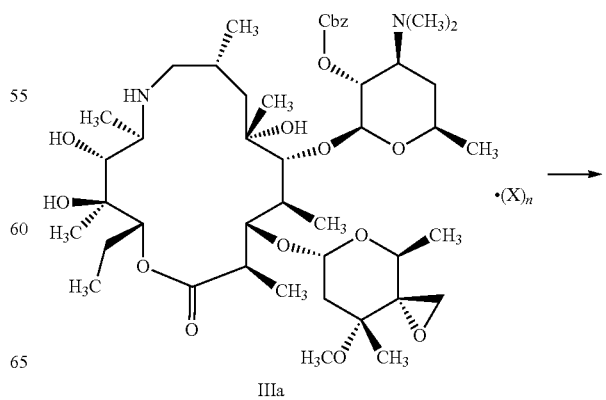

IIIa

-continued

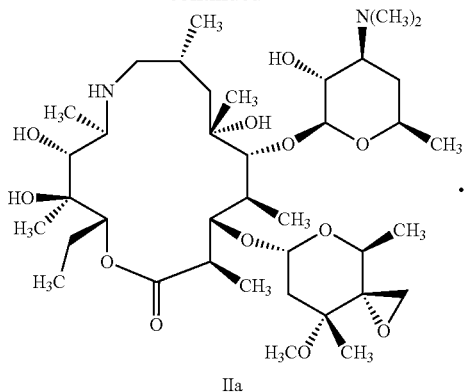

IIa wherein definitions of X and n are as defined in claim 8; the conditions of the de-protection reaction are the same as that of the method A of the method for preparing the compound represented by formula II.

The method for preparing the compound represented by formula II, preferably further comprises the following steps: in a halohydrocarbon solvent, subjecting the compound represented by formula III and an acid X to a salt formation reaction to produce the salt IIa of the compound represented by formula III;

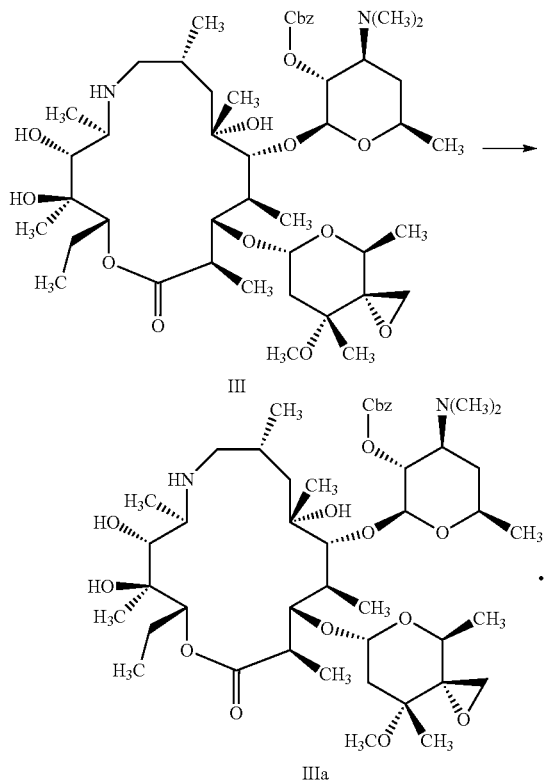

wherein, in IIa, the definition of X and n are the same as defined before.

The salt IIa of the compound represented by formula III is preferably trifluoroacetate IIIa1 of the compound represented by formula III:

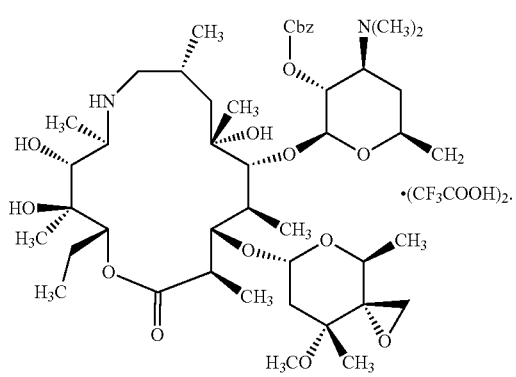

IIIa1

The method for preparing the trifluoroacetate IIIa1 of the compound represented by formula III preferably comprises the following steps: mixing a mixed solution of the compound represented by formula III and a halohydrocarbon solvent with trifluoroacetic acid, and performing the salt formation reaction;

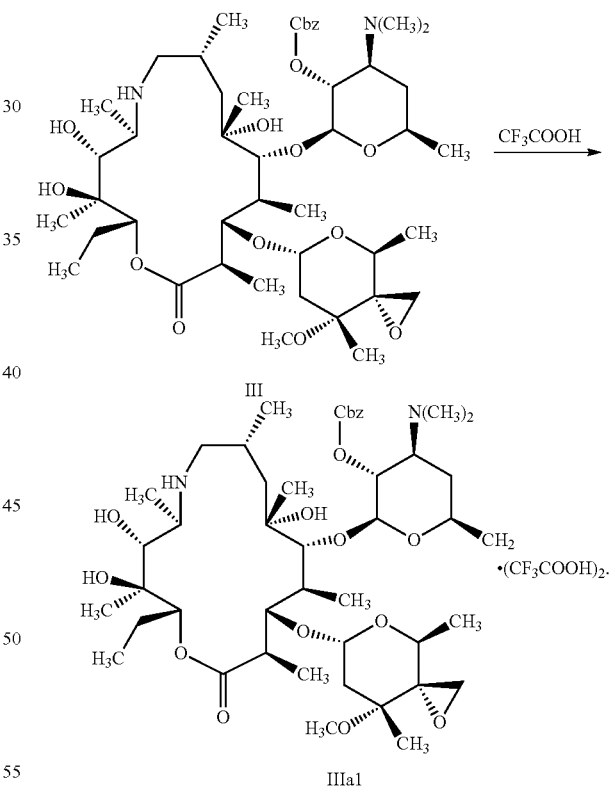

In the method for preparing the trifluoroacetate IIIa1 of the compound represented by formula III, the halohydrocarbon solvent is preferably dichloromethane. The amount of the halohydrocarbon solvent is not specifically limited, as long as the compound represented by formula III can be dissolved to obtain a transparent and clarified solution. Preferably, the volume to mass ratio of the halohydrocarbon solvent to the compound represented by formula III is from 2 mL/g to 20 mL/g, and more preferably from 3 mL/g to 10 mL/g. The mole ratio of the compound represented by formula III to the trifluoroacetic acid is preferably from 1:2 to 1:3, and more preferably from 1:2.05 to 1:2.25. The mixing temperature can be routine temperature in the art, preferably between 0 and 40° C., more preferably between 25 and 40° C., and most preferably between 30 and 40° C. The temperature and the duration of the salt formation reaction can be routine temperature and routine duration of this kind of reaction in the art. Preferably, the temperature of the salt formation reaction is the same as the temperature of mixing the mixed solution of the compound represented by formula III and halohydrocarbon solvent with the trifluoroacetic acid.

In the method for preparing the trifluoroacetate IIIa1 of the compound represented by formula III, the post-processing treatment is further included. The method and conditions of the post-processing treatment can be routine method and routine conditions of this kind of reactions in the art, and preferably comprise the following steps: adding an anti-solvent to the reaction solution after the salt formation reaction, mixing, and crystallizing. The anti-solvent is preferably isopropyl ether. The volume ratio of the halohydrocarbon solvent to the anti-solvent is preferably from 1:0.8 to 1:2, and more preferably from 1:1.3 to 1:1.5. The adding of the anti-solvent can be routine operation in the art, preferably dropwise adding. The temperature of the dropwise adding of the anti-solvent is preferably between 0 and 40° C., more preferably between 25 and 40° C., and most preferably between 30 and 40° C. During the adding of the anti-solvent, preferably, the adding is performed until the mixed solution turns turbid. After stirring and crystallizing for 0.5 to 1 hour, the remaining anti-solvent is added. The crystallization temperature can be routine temperature in the art, preferably between −5 and 40° C.

In a preferred embodiment of the present disclosure, in the method for preparing the trifluoroacetate IIIa1 of the compound represented by formula III, the trifluoroacetic acid is preferably in a form of trifluoroacetic acid halide solution to be added dropwise to the mixed solution of the compound represented by formula III and the halohydrocarbon solvent. In the trifluoroacetic acid halide solution, the amount of the halohydrocarbon solvent is not specifically limited.

In a preferred embodiment of the present disclosure, in the method for preparing the trifluoroacetate IIIa1 of the compound represented by formula III, the crystallization comprises an early stage of crystallization and a late stage of crystallization, wherein, the early stage of crystallization is carried out at a temperature between 10 and 40° C. for 0.5 to 3 hours (for example, 1 hour), and the late stage of crystallization is carried out at a temperature between −5 and 10° C. for 0.5 to 3 hours (for example, 1 hour).

In another preferred embodiment of the present disclosure, in the method for preparing the trifluoroacetate IIIa1 of the compound represented by formula III, after the completion of the crystallization, preferably, comprises filtration, washing (for example, using a mixed solvent of dichloromethane and isopropyl ether for washing), and drying (for example, vacuum drying at 45° C.) to obtain the trifluoroacetate IIIa1 of the compound represented by formula III.

Thus, in a preferred embodiment, the method for preparing salt (except for trifluoroacetate) of the compound represented by formula III can be referred to the above method for preparing the trifluoroacetate IIIa1 of the compound represented by formula III.

Thus, the present disclosure further provides a compound represented by formula IIIa1:

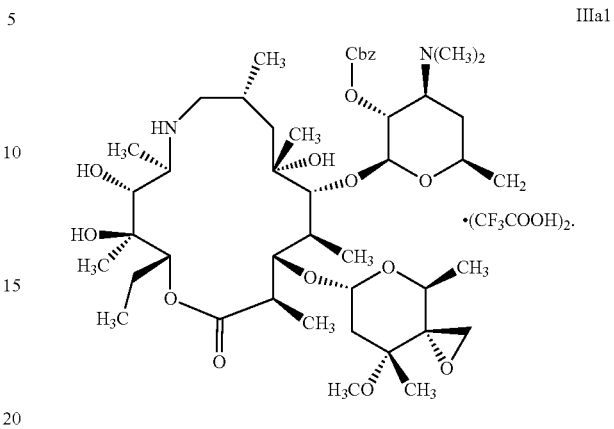

The present disclosure also provides a method for purifying tulathromycin represented by formula I, comprising the following steps: mixing crude tulathromycin represented by formula I with a solvent A, adding an anti-solvent, and crystallizing to obtain a product of tulathromycin represented by formula I; wherein the purity of the crude tulathromycin represented by formula I measured by HPLC is more than 65%; the solvent A is a mixed solvent of acetone and a $C_{1-3}$ alcohol; and the anti-solvent is water or a mixed solvent of water and acetone;

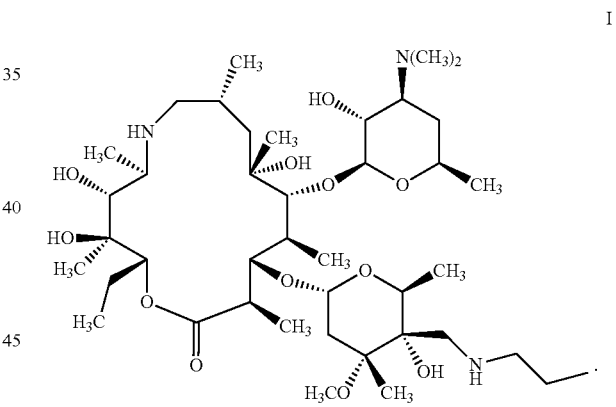

The purity of the crude tulathromycin represented by formula I measured by HPLC is preferably from 65 to 99.5% (for example, 99.2%).

The crude tulathromycin can be purchased on the market, or produced by routine method in the art, as long as the purity of which is above 65% measured by HPLC. Preferably, it is produced by the method illustrated above or produced by the method in examples 1-6 of the U.S. Pat. No. 6,825,327B2.

In the method of purification, the $C_{1-3}$ alcohol is preferably 1,2-propandiol. The amount of solvent A is not specifically limited, as long as the crude tulathromycin represented by formula I can be dissolved to obtain transparent and clarified solution. The volume to mass ratio of the solvent A to the crude tulathromycin represented by formula I is preferably from 2 mL/g to 50 mL/g, and more preferably from 2 mL/g to 30 mL/g. In the solvent A, the ratio of the amount of the acetone and the amount of the $C_{1-3}$ alcohol is not specifically limited.

In the method of purification, when the anti-solvent is a mixed solvent of water and acetone, the volume ratio of the water and the acetone is preferably from 0.5:1 to 3:1. The adding of anti-solvent can be routine operations in the art, preferably dropwise adding. The temperature of adding anti-solvent can be routine temperature in the art, preferably between 35 and 45° C. The amount of the anti-solvent is not specifically limited, as long as tulathromycin represented by formula I can be precipitated; preferably, the volume to mass ratio of the anti-solvent to the crude tulathromycin represented by formula I is from 2 mL/g to 60 mL/g. When adding the anti-solvent, the adding is preferably finished until the solution A containing tulathromycin represented by formula I turns turbid, the resulting mixture is stirred and crystalline grain culturing is carried out for 10 to 30 minutes, and the remaining anti-solvent is added In the method of purification, the temperature of crystallization can be routine temperature in the art, preferably between 0 and 45° C. The duration of the crystallization can be routine duration in the art, preferably from 1 to 6 hours, and more preferably from 1 to 3 hours (for example, 2 hours).

In a preferred embodiment of the present disclosure, in the method of purification, the crystallization comprises an early stage of crystallization and a late stage of crystallization, wherein the early stage of crystallization is carried out at a temperature between 35 and 45° C. for 0.5 to 3 hours (for example, 1 hour), and the late stage of crystallization is carried out at a temperature between 0 and 35° C. (for example, between 0 and 10° C.) for 0.5 to 3 hours (for example, 1 hour).

In another preferred embodiment of the present disclosure, in the method of purification, after the crystallization, filtration, washing and drying are preferably carried out to obtain tulathromycin product represented by formula I.

In a preferred embodiment of the present disclosure, if it is desired to obtain high-purity (for example, the purity measured by HPLC is above 99%) tulathromycin product represented by formula I, tulathromycin product obtained by one purification is subjected to the method of purification again (once, or more than once).

Without prejudice to the common sense in the art, the above preferred conditions can be arbitrarily combined to obtain the preferred embodiments of the present disclosure.

All the reagents and raw materials used in the present disclosure can be purchased on the market.

In the present disclosure, the room temperature refers to the ambient temperature, which is generally between 10 and 30° C.

In the present disclosure, the temperatures of adding the materials, the mixing, and the like refer to the temperature of the reaction system (or reaction solution).

The positive and progressive effect of the present invention lies in:

the purity of tulathromycin obtained by the method of the present disclosure is high, and the purity measured by HPLC reaches above 99%, which meets the purity requirement of pharmaceutical preparation, and is beneficial to increase the biological activity and ensure the curative efficacy; at the same time, the method of the present disclosure has high yield, simple operations and is more suitable for industrial production.

DETAILED DESCRIPTION

In the following examples, the HLPC content refers to the purity measured by HPLC.

EXAMPLE 1

Preparation of the Compound Represented by Formula V 25 g of dihydroerythromycin and 350 mL of dichloromethane were added to a 1L three-necked flask, stirred, and dissolved. Nitrogen was filled in the flask for protection, and the temperature was cooled to 0 to 10° C. by an ice-salt water bath. A mixed solution of 12.2 mL of carbobenzoxy chloride and 50 mL of dichloromethane was added dropwise over 20 minutes, during which the internal temperature was kept between 0 and 10° C. The reaction was traced by TLC+HPLC until the reaction was completed, and the duration of the reaction was 3 hours. 125 mL of saturated $NaHCO_3$ aqueous solution was added to quench the reaction. The organic layer was separated from the water layer, and 50 mL of dichloromethane was added to the water layer for one more extraction. The organic layers were combined, washed with 100 mL of saturated sodium bicarbonate solution once, and dried with anhydrous sodium sulfate. The mixture was filtered, concentrated under reduced pressure at a temperature between 35 and 40° C., and drained with an oil pump to give 29.1 g of a bubble compound represented by formula V, MS(ESI)868.53.

EXAMPLE 2

Preparation of the Compound Represented by Formula IV

The bubble compound represented by formula V produced in the Example 1 was dissolved with 150 mL of dichloromethane, and 50 mL of DMSO was added under stirring. Nitrogen was filled in for protection and the mixture was cooled to −75° C. with liquid nitrogen. A mixed solution of 11.5 mL of trifluoroacetic anhydride and 25 mL of $CH_2Cl_2$ was added dropwise, reaction was carried out for 45 minutes, and the internal temperature was kept between −65 and −75° C. Then a mixed solution of 25 mL of triethylamine and 25 mL of $CH_2Cl_2$ was added dropwise, reaction was carried out for 30 minutes, and the temperature was kept between −65 and −75° C. Water was added to quench the reaction. The mixture was stratified, and the water layer was separated out. The organic layer was washed with 100 mL of saturated salt water once. After stratification, anhydrous sodium sulfate was added to the organic layer for drying. The mixture was filtered, concentrated under reduced pressure, and drained with an oil pump to give 24.3 g of a bubble compound represented by formula IV, MS(ESI)866.51.

EXAMPLE 3

Preparation of the Compound Represented by Formula III 17.6 g (0.11 mol) of trimethylsulfonium bromide was added to a 1000 mL three-necked flask. Under nitrogen protection and mechanical agitation, 150 mL of THF was added and the temperature was cooled to −15° C. with liquid nitrogen. 12.5 g (0.11 mol) of potassium tert-butoxide was added, the internal temperature was kept between −15 and −5° C., and the reaction was carried out for 1 hour under stirring. The temperature was then cooled to −75° C., a solution of 24.3 g (0.028 ml) of the compound represented by formula IV obtained in Example 2 and 250 mL of $CH_2Cl_2$ was added dropwise for 1 hour, and the temperature was kept between −75 and −65° C. After the adding, the reaction was carried out for 2 hours while the temperature was kept between −75 and −65° C. The reaction was traced by HPLC until the completion of the reaction. Ammonium chloride aqueous solution was added to quench the reaction. The temperature of the reaction solution was raised to room temperature, and the water layer and the organic layer were separated. The water layer was extracted with $CH_2Cl_2$ once. The organic layers were combined and washed with saturated salt water once. Anhydrous sodium sulfate was added to the organic layer for drying. The mixture was filtered, concentrated at a temperature between 35 and 40° C. to almost dry, and drained with an oil pump for 1 h to give 24.7 g of a bubble compound represented by formula III, MS(ESI)880.53.

EXAMPLE 4

Preparation of Trifluoroacetate of the Compound Represented by Formula III 24.7 g of the bubble compound produced by Example 3 was dissolved in 80 mL of $CH_2Cl_2$, and a mixed solution of 7.2 g trifluoroacetic acid and 20 mL of $CH_2Cl_2$ was added dropwise at temperature between 25 and 35° C. Then 150 mL of isopropyl ether was added dropwise at 30° C.; the solution turned turbid when about 100 mL isopropyl ether was added, and the adding was stopped. The mixture was slowly stirred for 0.5 hour, and the remaining isopropyl ether was added dropwise. The mixture was stirred at 30° C. to crystallization for 1 hour, followed by cooling crystallization in an ice-water bath (between −5 and 0° C.) for 1 hour. After filtration, the filter cake was washed with a mixed solvent of 10 mL of $CH_2Cl_2$ and 15 mL of isopropyl ether, and the filter cake was subjected to vacuum drying at 45° C. to give 26.2 g of a loose white solid, i.e., trifluoroacetate of the compound represented by formula III with a purity of 88.2% measured by HPLC, $^1$H-NMR(400 MHz, DMSO); δ=10.85 (s, 1H); 8.70(s, 1H); 8.38(t, J=9.7 Hz, 1H); 7.38(s, 5H); 6.08(s, 1H); 5.18(d, J=12.3 Hz, 1H); 5.06(d, J=12.2 Hz, 1H); 5.01(d, J=3.9 Hz, 1H); 4.90(dd, J=10.1 Hz, 2.0 Hz, 1H); 4.70(q, J=6.5 Hz, 1H); 4.60-4.67(m, 2H); 4.00(s, 1H); 3.67-3.72(m, 1H); 3.55-3.63(m, 1H); 3.47(d, J=6.0, 1H); 3.41(s, 1H); 3.23-3.30(m, 4H); 3.00-3.06(m, 1H); 2.67-2.76 (m, 10H); 2.59-2.64(m, 1H); 2.39(d, J=14.8 Hz, 1H); 2.13-2.15(m, 1H); 1.73-1.89(m, 4H); 1.58-1.67(m, 1H); 1.35-1.44(m, 1H); 1.24-1.31(m, 8H); 1.15(d, J=5.8 Hz, 3H); 1.10(d, J=6.0, 3H); 1.07(s, 3H); 1.01-1.03(m, 3H); 0.93-0.94 (m, 6H); 0.82(t, J=7.4 Hz, 3H); 0.74(d, J=7.1 Hz, 3H). MS(ESI)880.53.

Results of experiments under other conditions:

| Number | 1 | 2 | 3 |
|---|---|---|---|
| Amount of compound of formula III | 2 g | 5 g | 5 g |
| Compound of formula III: trifluoroacetic acid (mole ratio) | 1:2 | 1:2.5 | 1:3 |
| Amount of $CH_2Cl_2$ | 20 ml | 50 ml | 50 ml |
| Amount of isopropyl ether | 16 ml | 100 ml | 60 ml |
| Reaction temperature | 30-35° C. | 0-10° C. | 35-40° C. |
| Crystallization temperature | Crystallizing at 30-35° C. for 1 hour; then crystalizing at −5~0° C. for 1 hour | Crystallizing at 10-20° C. for 1 hour; then crystallizing at −5~0° C. for 1 hour | Crystallizing at 30-40° C. for 1 hour; then crystallizing at 0~10° C. for 1 hour |
| Amount of compound of formula IIIa1 | 2.0 g | 5.4 g | 5.3 g |
| HPLC purity of compound of formula IIIa1 | 90.1% | 86.1% | 88.5% |

EXAMPLE 5

Preparation of the Compound Represented by Formula II 15 g of trifluoroacetate of the compound represented by formula III produced in Example 4 was dissolved in 150 mL of methanol under stirring. Under the protection of nitrogen, 7.5 g of ammonium formate was added. After ammonium formate was absolutely dissolved, 1.1 g of 10% Pd/C was added, and the reaction was carried out at temperature between 20 and 25° C. The reaction was traced by HPLC until the reaction was completed, which lasted for about 2 to 3 hours. The mixture was filtered, the filter cake was washed with methanol and the filtrate was concentrated at 40° C. under reduced pressure. 40 mL of water and 60 mL of dichloromethane were added to dissolve the mixture under stirring. 2N sodium hydroxide aqueous solution was used to adjust the pH to between 9 and 10 under stirring for 30 minutes. After stratification, the upper water layer was extracted with 40 mL of dichloromethane, the organic layers were combined and washed with saturated salt water. After stratification, anhydrous sodium sulfate was added to the organic layer for drying. The mixture was filtered, concentrated under reduced pressure at a temperature between 35 and 40° C., and drained with an oil pump to give 11.7 g of a bubble compound represented by formula II with a purity of 86.1% measured by HPLC, MS(ESI)746.49.

Results of experiments under other conditions:

| Number | 1 | 2 | 3 |
|---|---|---|---|
| Amount of trifluoroacetate of formula III | 5 g | 5 g | 5 g |
| Amount of Pd/C | 0.5 g of 5% Pd/C | 0.5 g of 10% Pd/C | 0.5 g of 15% Pd/C |
| Solvent and the amount thereof used in reaction | Ethanol, 50 mL | Isopropanol, 50 mL | Methanol, 50 mL |
| Temperature and duration of the reaction | 20-25° C., 3 h | 20-25° C., 3 h | 20-25° C., 3 h |
| Mass of compound of formula II | 3.7 g | 3.4 g | 3.8 g |
| HPLC purity of the compound of formula II | 84.6% | 82.2% | 86.7% |

EXAMPLE 6

Preparation of the Compound Represented by Formula II 5 g of the compound represented by formula III produced in Example 3 was dissolved in 50 mL of methanol under stirring. Under the protection of nitrogen, 2.5 g of ammonium formate was added. After ammonium formate was absolutely dissolved, 0.4 g of 10% Pd/C was added, and the reaction was carried out at temperature between 20 and 25° C. The reaction was traced by HPLC until the reaction was completed, which lasted for about 2 to 3 hours. The mixture was filtered, the filter cake was washed with methanol and the filtrate was concentrated at 40° C. under reduced pressure. 20 mL of water and 50 mL of dichloromethane were added to dissolve the mixture under stirring. 2N sodium hydroxide aqueous solution was used to adjust the pH to between 9 and 10 under stirring for 30 minutes. After stratification, the upper water layer was extracted with 20 mL of dichloromethane, the organic layers were combined and washed with saturated salt water. After stratification, anhydrous sodium sulfate was added to the organic layer for drying. The mixture was filtered, concentrated under reduced pressure at a temperature between 35 and 40° C., and drained with an oil pump to give 4.1 g of a bubble compound represented by formula II with a purity of 78.9% measured by HPLC, MS(ESI)746.49.

EXAMPLE 7

Preparation of the Compound Represented by Formula I 11.7 g of the bubble compound represented by formula II produced in Example 5 was dissolved in 6.0 mL of 1,2-propandiol and 12 mL of n-propylamine. Under the protection of nitrogen, the reaction was carried out at temperature between 45 and 55° C. and traced by HPLC until the reaction was completed, which lasted for 20 hours. The mixture was concentrated at 40° C. under reduced pressure until no liquid drop to give an oil-like product containing crude 1,2-propaniol tulathromycin with a tulathromycin content of 78.3% measured by HPLC.

Results of experiments under other conditions:

| Number | Compound of formula II: n-propyl-amine (mole ratio) | Temperature of the reaction (° C.) | Duration of the reaction | HPLC purity of tulathromycin |
|---|---|---|---|---|
| 1 | 1:5 | 55-65° C. | 16 h | 77.3% |
| 2 | 1:20 | 45-50° C. | 26 h | 75.8% |
| 3 | 1:30 | 45-50° C. | 35 h | 73.9% |

EXAMPLE 8

65 mL of acetone was added to the oil-like crude 1,2-propandiol tulathromycin produced in Example 7. The mixture was disposed in water bath at about 40° C. and 85 mL of water was slowly added dropwise. When the crystallization liquid turned turbid, the adding was stopped, and crystalline grain culturing was carried out for 10 minutes under stirring, and then the remaining water was added. After the adding of water, the mixture was hold in a water bath at temperature between 35 and 40° C. for 1 hour with stirring. The mixture was cooled to 0 to 10° C. in an ice-water bath, and quickly stirred for 1 hour. After filtration, the resulting solid was washed with an appropriate amount of 40% acetone aqueous solution to give a loose white solid, which was the wet product of tulathromycin after first crystallization, with a content of 95.8% measured by HPLC, MS(ESI)805.57.

EXAMPLE 9

25 mL of acetone and 3.0 mL of 1,2-propandiol were added and mixed with 5.0 g of the first crystallization product of tulathromycin obtained in Example 8. The mixture was hold in water bath at 40° C. with stirring for dissolution. An anti-solvent of 25 mL of acetone and 60 mL of water was slowly added dropwise. When the crystallization liquid turned turbid, the adding was stopped, and crystalline grain culturing was carried out for 10 minutes under stirring, and then the remaining anti-solvent was added. After the adding of anti-solvent, the mixture was hold in a water bath at 40° C. for 1 hour with stirring. The mixture was cooled to 0 to 10° C. in an ice-water bath, and quickly stirred for 1 hour. After filtration, the resulting solid was washed with an appropriate amount of 40% acetone aqueous solution to give a wet solid of tulathromycin crystal, with a purity of 99.2% measured by HPLC, MS(ESI)805.57.

Results of experiments under other conditions.

Therein, (1) tulathromycin product produced in Example 7 was dried to obtain a dried tulathromycin product by drying; (2) mixed solvent and amount; (3) anti-solvent and amount; (4) crystallization process; (5) yield of recrystallization; (6) purity of tulathromycin product obtained after the recrystallization measured by HPLC.

| Number | 1 | 2 | 3 | 4 |
|---|---|---|---|---|
| (1) | 1 g | 1 g | 1 g | 1 g |
| (2) | 2.5 mL (2 mL of acetone and 0.5 mL of 1,2-propandiol) | 11 mL (10 mL of acetone and 1 mL of 1,2-propandiol) | 15 mL (10 mL of acetone and 5 mL of 1,2-propandiol) | 30 mL (25 mL of acetone and 5 mL of 1,2-propandiol) |
| (3) | 2 mL of water | 50 mL (40 mL of water and 10 mL of acetone) | 47 mL (27 mL water and 20 mL of acetone) | 45 mL (25 mL water and 20 mL of acetone) |
| (4) | Slowly add the anti-solvent dropwise; stop adding when the crystallization liquid turn turbid; stir and culture the crystalline grain for 10 minutes; add the remaining water; stir and | Slowly add the anti-solvent dropwise; stop adding when the crystallization liquid turn turbid; stir and culture the crystalline grain for 30 minutes; add the remaining mixed solution; stir and incubate in a water bath | Slowly add the anti-solvent dropwise; stop adding when the crystallization liquid turn turbid; stir and culture the crystalline grain for 20 minutes; add the remaining mixed solution; stir and incubate in a water bath | Slowly add the anti-solvent dropwise; stop adding when the crystallization liquid turn turbid; stir and culture the crystalline grain for 20 minutes; add the remaining mixed solution; stir and incubate in a water bath |

-continued

| Number | 1 | 2 | 3 | 4 |
|---|---|---|---|---|
|  | incubate in a water bath at 40° C. for 1 hour. | at 45° C. for 3 hours; cool to 0-10° C. in ice-water bath and stir for 3 hours. | at 35° C. for 1 hour; cool to 0-5° C. in ice-water bath and stir for 1 hour. | at 35° C. for 1 hour; cool to 10° C. in ice-water bath and stir for 1 hour. |
| (5) | 98.2% | 96.4% | 95.3% | 93.7% |
| (6) | 97.6% | 99.0% | 99.3% | 99.5% |

EXAMPLE 10

2.5 mL of acetone and 0.3 mL of 1,2-propandiol were added to 0.5 g of tulathromycin product represented by formula I (obtained in Example 9 with a purity of 99.2% measured by HPLC). The mixture was hold in water bath at 40° C. with stirring for dissolution. A mixed solution of 2.5 mL of acetone and 6 mL of water was slowly added, dropwise. When the crystallization liquid turned turbid, the adding was stopped, and crystalline grain culturing was carried out for 10 minutes under stirring, and then the remaining mixed solution was added. After the adding of mixed solution, the mixture was hold in a water bath at 40° C. for 1 hour with stirring. The mixture was cooled to 0 to 10° C. in an ice-water bath and stirred for 1 hour. After filtration, the resulting solid was washed with an appropriate amount of 40% acetone aqueous solution to give a wet solid of tulathromycin crystal, with a purity of 99.5% measured by HPLC.

EXAMPLE 11

5.0 mL of acetone and 0.6 mL of 1,2-propandiol were added to 1.0 g of crude tulathromycin with a purity of 68.9% measured by HPLC (prepared by the method in Example 1-6 of the U.S. Pat. No. 6,825,327B2). The mixture was hold in water bath at 41° C. with stirring for dissolution. A mixed solution of 5 mL of acetone and 12 mL of water was slowly added, dropwise. When the crystallization liquid turned turbid, the adding was stopped, and crystalline grain culturing was carried out for 10 minutes under stirring, and then the remaining mixed solution was added. After the adding of mixed solution, the mixture was hold in a water bath at 40° C. for 1 hour with stirring. The mixture was cooled to 0 to 10° C. in an ice-water bath and stirred for 1 hour. After filtration, the resulting solid was washed with an appropriate amount of 40% acetone aqueous solution to give a wet solid of tulathromycin crystal with a purity of 95.2% measured by HPLC, MS(ESI)805.57.

EXAMPLE 12

5 mL of acetone was added to 0.5 g of tulathromycin represented by formula I with a purity of 99.2% measured by HPLC obtained in Example 7. The mixture was hold in water bath at 35° C. with stirring for dissolution. 7.5 mL of water was slowly added, dropwise. When the crystallization liquid turned turbid, the adding was stopped, and crystalline grain culturing was carried out for 10 minutes under stirring, and then the remaining water was added. After the adding of mixed solution, the mixture was cooled for 1 hour with stirring. The mixture was cooled to 0 to 10° C. in an ice-water bath and stirred for 1 hour. After filtration, the resulting solid was washed with an appropriate amount of 40% acetone aqueous solution to give a wet solid of tulathromycin crystal with a purity of 92.4% measured by HPLC.

EXAMPLE 13

0.5 mL of 1,2-propandiol and 5 mL of methanol were added to 0.5 g of tulathromycin represented by formula I with a purity of 99.2% measured by HPLC obtained in Example 7. The mixture was hold in water bath at 40° C. with stirring for dissolution. 6 mL of water was slowly added, dropwise. When the crystallization liquid turned turbid, the adding was stopped, and crystalline grain culturing was carried out for 10 minutes under stirring, and then the remaining water was added. After the adding of mixed solution, the mixture was hold in a water bath at 40° C. for 1 hour with stirring. The mixture was cooled to 0 to 10° C. in an ice-water bath and stirred for 1 hour. After filtration, the resulting solid was washed with an appropriate amount of 40% acetone aqueous solution to give a wet solid of tulathromycin crystal with a purity of 94.6% measured by HPLC.

COMPARATIVE EXAMPLE 1

5 g of the bubble compound represented by formula II produced by Example 5 was dissolved in 2.5 mL of isopropanol and 5 mL of n-propylamine. Under the protection of nitrogen, the reaction was carried out at temperature between 45 and 55° C. and traced by HPLC until the reaction was completed, which lasted for 20 hours. The mixture was concentrated at 40° C. under reduced pressure until no liquid drop to give an oil-like crude tulathromycin with a tulathromycin content of 60.3% measured by HPLC.

COMPARATIVE EXAMPLE 2

3 g of the bubble compound represented by formula II produced by Example 5 was mixed with 15 mL of isopropanol and 6.1 g of n-propylamine. The mixture was reacted at a temperature between 50 and 55° C. for 30 hours, and then was concentrated to about 8 mL in a water bath at 50° C. under vacuum. The sample was taken and measured by HPLC, and the purity of the target compound tulathromycin was 68.9%.

Although specific embodiments of the present invention have been described above, those skilled in the art should understand that these are merely illustrative examples, numerous variations or modifications may be made to these embodiments without departing from the principles and spirit of the present invention. Therefore, the protection scope of the present invention is defined by the appended claims.

What is claimed is:
1. A method for preparing tulathromycin represented by formula I, comprising the following steps: subjecting a compound represented by formula II and n-propylamine to ring-opening addition reaction shown below in an organic solvent to produce tulathromycin represented by formula I; wherein the organic solvent is 1,2-propandiol;

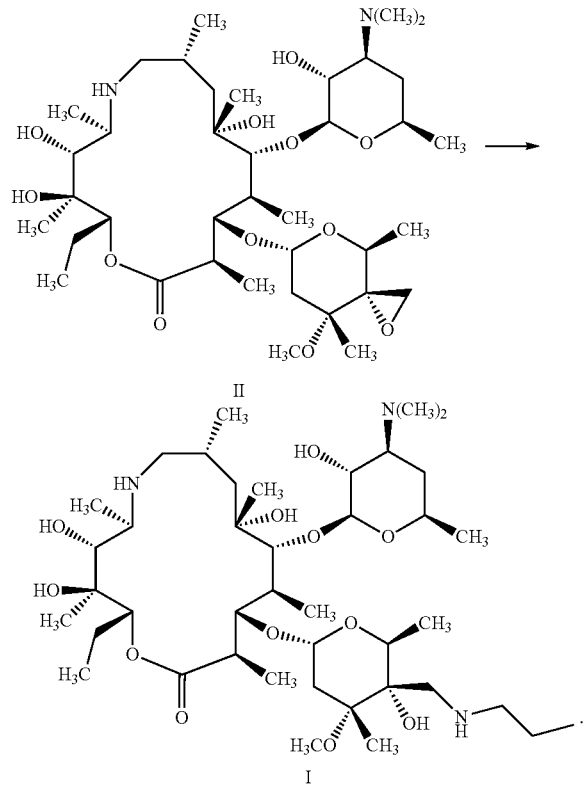

2. The method according to claim 1, wherein the mole ratio of the compound represented by formula II to n-propylamine is from 1:5 to 1:30; the temperature of the ring-opening addition reaction is between 30 and 90° C.; the duration of the ring-opening addition reaction is from 15 to 40 hours; the method for preparing tulathromycin represented by formula I comprises the following steps: mixing a mixed solution of the compound represented by formula II and the organic solvent with n-propylamine, and performing the ring-opening addition reaction; the ring-opening addition reaction is performed in the condition of gas protection; the gas for the gas protection is nitrogen.

3. The method according to claim 1, which further comprises a post-processing treatment after the completion of the ring-opening addition reaction; the post-processing treatment comprises the following steps: removing n-propylamine and the organic solvent after the completion of the ring-opening addition reaction to obtain crude tulathromycin represented by formula I; and performing recrystallization to obtain tulathromycin represented by formula I.

4. The method according to claim 3, wherein method of the removing n-propylamine and the organic solvent in the post-processing treatment is concentration under reduced pressure; and/or, the recrystallization comprises the following steps: mixing the crude tulathromycin represented by formula I with a solvent A, then adding an anti-solvent, crystallizing to obtain a product of tulathromycin represented by formula I; wherein, the solvent A is a mixed solvent of acetone and $C_{1-3}$ alcohol; and the anti-solvent is water or a mixed solvent of water and acetone.

5. The method according to claim 4, wherein the $C_{1-3}$ alcohol in recrystallization is 1,2-propandiol; and/or, the volume to mass ratio of the solvent A to the crude tulathromycin represented by formula I is from 2 mL/g to 50 mL/g; and/or, the adding of the anti-solvent is dropwise adding; and/or, the temperature of adding the anti-solvent is between 35 and 45° C.; and/or, the volume to mass ratio of the anti-solvent to the crude tulathromycin represented by formula I is from 2 mL/g to 60 mL/g; and/or, when the anti-solvent is the mixed solvent of water and acetone, the volume ratio of the water to acetone is from 0.5:1 to 3:1.

6. The method according to claim 4, wherein during adding the anti-solvent in the recrystallization, the adding is finished until the solution A containing tulathromycin represented by formula I turns turbid, the resulting mixture is stirred and crystalline grain culturing is carried out for 10 to 30 minutes, and the remaining anti-solvent is added; the temperature of the crystallization is between 0 and 45° C.; and the duration of the crystallization is from 1 to 6 hours.

7. The method according to claim 4, wherein during the recrystallization, the crystallization comprises an early stage of crystallization and a late stage of crystallization, wherein, the early stage of crystallization is carried out at a temperature between 35 and 45° C. for 0.5 to 3 hours, and the late stage of crystallization is carried out at a temperature between 0 and 35° C. for 0.5 to 3 hours.

8. The method according to claim 1, wherein the method for preparing the compound represented by formula I further comprises the following method A or method B:
the method A comprises the following steps: with the action of a catalyst and a hydrogen source, subjecting a compound represented by formula III to de-protection reaction shown below in the organic solvent to produce the compound represented by formula II;

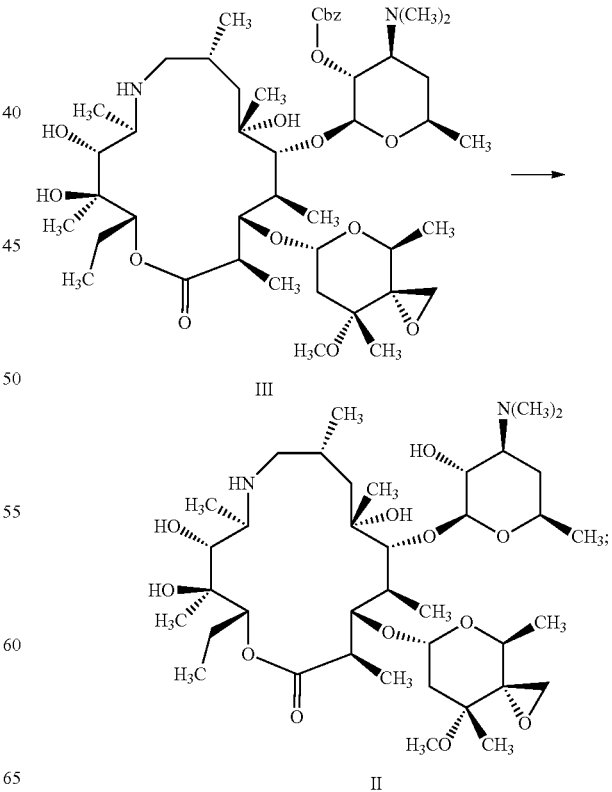

the method B comprises the following steps: in a mixed solvent of water and a non-polar organic solvent, subjecting a salt IIa of the compound represented by formula II and a base to acid-base neutralization reaction to produce the compound represented by formula II;

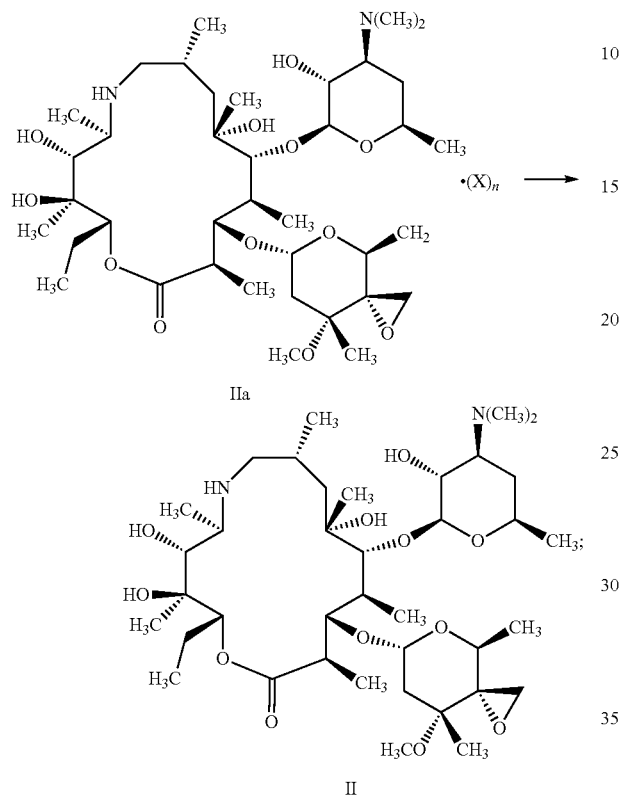

and wherein in the compound IIa, X is an organic acid or an inorganic acid, and n is 1, 2 or 3.

9. The method according to claim 8, wherein
in the method A, the organic solvent is a $C_{1-3}$ alcohol and/or a ketone; the $C_{1-3}$ alcohol is selected from the group consisting of methanol, ethanol and isopropanol, or a mixture thereof; the ketone is acetone; the catalyst is palladium-carbon; the mass percentage of palladium in the palladium-carbon is from 3 to 20%; the percentage refers to the percentage of the mass of palladium in the total mass of the palladium-carbon; the hydrogen source is ammonium formate; the amount of the catalyst is 5% to 15% of the mass of the compound represented by formula III; the amount of the hydrogen source is more than 1 fold of the mole quantity of the compound represented by formula II; the temperature of the de-protection reaction is between 20 and 25° C.; the duration of the de-protection reaction is from 1 to 6 hours; the method for preparing the compound represented by formula II comprises the following steps: mixing the mixed solution of the compound represented by formula III and the organic solvent with the hydrogen source and the catalyst, performing the de-protection reaction; the de-protection reaction is performed in the condition of gas protection; the gas for the gas protection is nitrogen;
and/or, in the method B, the organic acid is trifluoroacetic acid; the non-polar organic solvent is a halocarbon solvent; the halocarbon solvent is dichloromethane and/or trichloromethane; the base is an inorganic base; and the inorganic base is selected from the group consisting of potassium carbonate, sodium carbonate, sodium hydroxide and potassium carbonate, or a mixture thereof.

10. The method according to claim 8, wherein in the method A, the method for preparing the compound represented by formula II further comprises the following steps: in the organic solution, with the action of the base, subjecting trimethylsulfonium halide and a compound represented by formula IV to epoxidation reaction shown below to produce the compound represented by formula III;

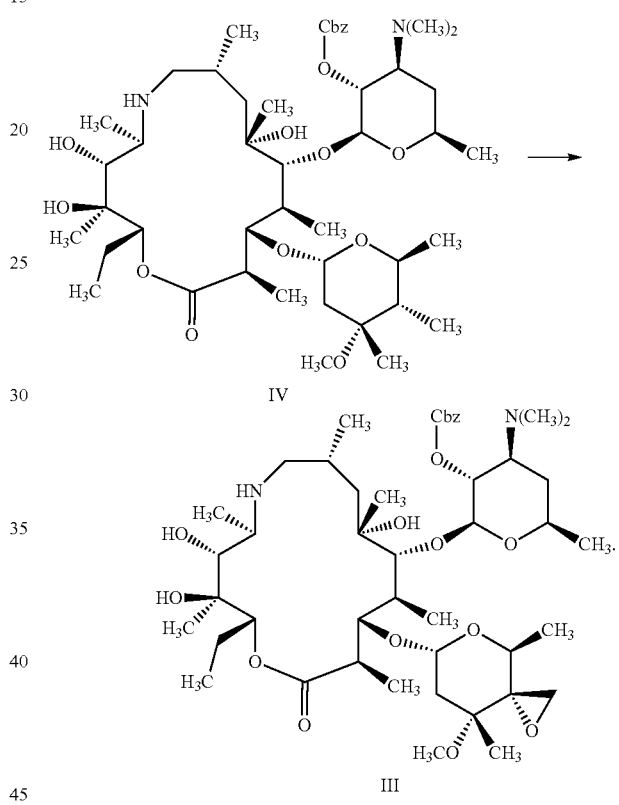

11. The method according to claim 10, wherein in the method for preparing the compound represented by formula III, the trimethylsulfonium halide is trimethylsulfonium bromide; the organic solvent is an ether; the ether is tetrahydrofuran; the base is potassium tert-butoxide; the mole ratio of the trimethylsulfonium halide to the compound represented by formula IV is from 2:1 to 10:1; the mole ratio of the trimethylsulfonium halide to the base is from 1:1 to 1.2:1; the temperature for mixing the trimethylsulfonium halide with the base is between −15 and −5° C.; after mixing the trimethylsulfonium halide with the base, stirring the mixed solution at a temperature between −15 and −5° C. for 0.5 to 3 hours; after mixing the mixed solution of trimethylsulfonium halide and the organic solvent with the base, controlling the temperature of the reaction system between −75 and −65° C., and then adding an organic solution of the compound represented by formula IV; the organic solvent in the organic solution of the compound represented by formula IV is a halohydrocarbon solvent; the halohydrocarbon solvent is dichloromethane; the temperature of the epoxidation reaction is between −75 and −65° C.; the method for preparing the compound represented by formula III comprises the following steps: mixing the mixed solution of trimethylsulfonium halide and the organic solvent with the base, adding the organic solvent of the compound represented by formula IV, and performing the epoxidation reaction; and the epoxidation reaction is performed in the condition of gas protection, wherein the gas for the gas protection is nitrogen.

12. The method according to claim 8, wherein in the method B, the method for preparing the compound represented by formula II further comprises the following steps: in the organic solvent, with the action of the catalyst and the hydrogen source, subjecting a salt IIIa of the compound represented by formula III to the de-protection reaction to produce the salt IIa of the compound represented by formula II;

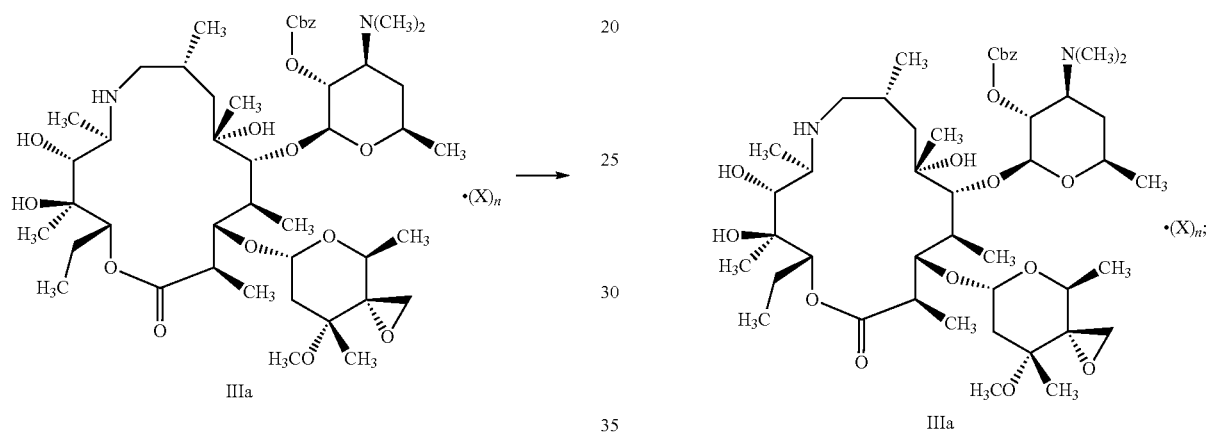

wherein definitions of X and n are as defined in claim 8; the conditions of the de-protection reaction are the same as that of the method A of the method for preparing the compound represented by formula II.

13. The method according to claim 12, wherein the method for preparing the salt of the compound represented by formula II further comprises the following steps: in a halohydrocarbon solvent, subjecting the compound represented by formula III and an acid X to salt formation reaction to produce the salt IIIa of the compound represented by formula III;

wherein X is an organic acid or an inorganic acid, and n is 1, 2 or 3, and the salt IIIa of the compound represented by formula III is a trifluoroacetate IIIa1 of the compound represented by formula III:

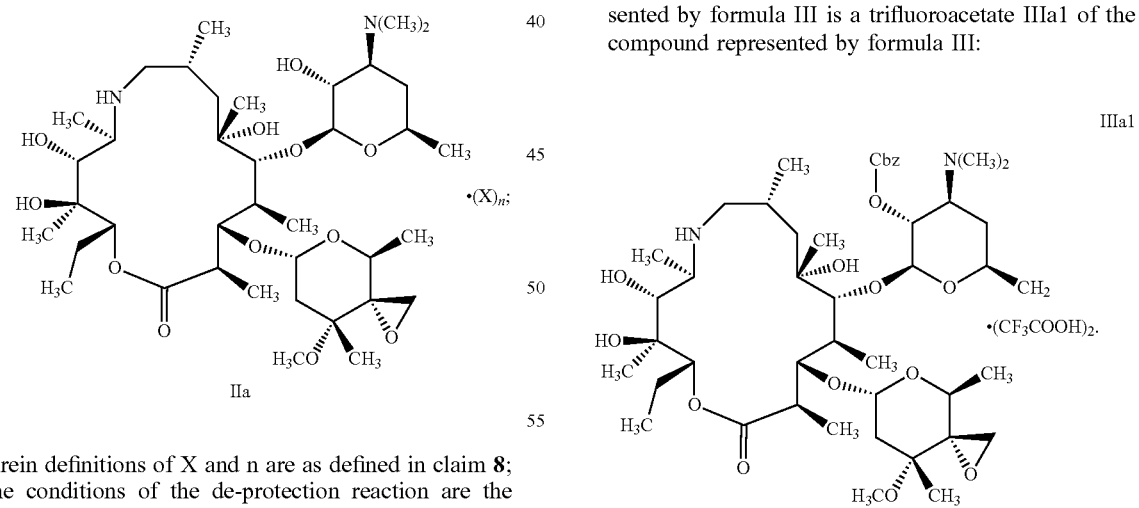

14. The method according to claim 13, wherein the method for preparing the trifluoroacetate IIIa1 of the compound represented by formula III further comprises the following steps: mixing a mixed solution of the compound represented by formula III and a halohydrocarbon solvent with trifluoroacetic acid, and performing the salt formation reaction;

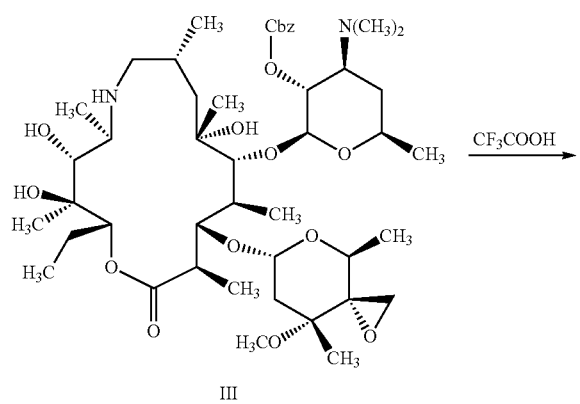

III

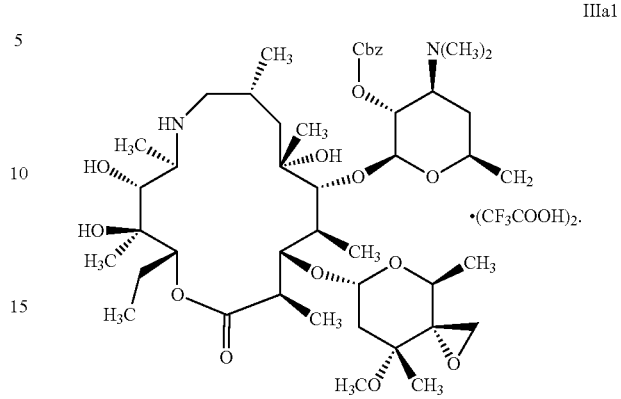

IIIa1

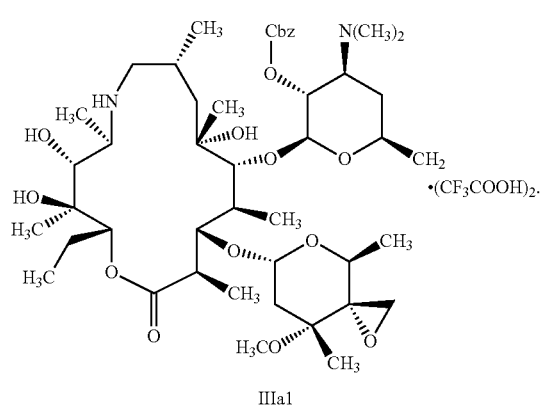

IIIa1

15. The method according to claim 14, wherein in the method for preparing the trifluoroacetate IIIa1 of the compound represented by formula III, the halohydrocarbon solvent is dichloromethane; and/or, the mole ratio of the compound represented by formula III to trifluoroacetic acid is from 1:2 to 1:3; and/or, the temperature of the mixing is between 0 and 40° C.

16. The method according to claim 14, wherein the method for preparing the trifluoroacetate IIIa1 of the compound represented by formula III further comprises a post-processing treatment; and the post-processing treatment comprises the following steps: adding an anti-solvent to the reaction solution after the salt formation reaction, mixing, and crystallizing; the anti-solvent is isopropyl ether; the volume ratio of the halohydrocarbon solvent to the anti-solvent is from 1:0.8 to 1:2; the adding of the anti-solvent is dropwise adding; the temperature of the dropwise adding of the anti-solvent is between 0 and 40° C.; the temperature of the crystallization is between −5 and 40° C.

17. A compound represented by formula IIIa1:

18. A method for purifying tulathromycin represented by formula I, comprising the following steps: mixing a crude tulathromycin represented by formula I with a solvent A, adding an anti-solvent, and crystallizing to obtain a product of tulathromycin represented by formula I; wherein the purity of the crude tulathromycin represented by formula I measured by HPLC is more than 65%; the solvent A is a mixed solvent of acetone and a $C_{1-3}$ alcohol; and the anti-solvent is water or a mixed solvent of water and acetone;

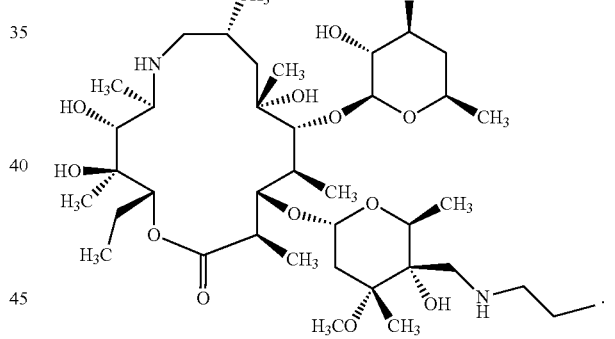

I

19. The method according to claim 18, wherein the purity of the crude tulathromycin represented by formula I measured by HPLC is from 65 to 99.5%; and/or, the $C_{1-3}$ alcohol is 1,2-propandiol; and/or, the volume to mass ratio of the solvent A to the crude tulathromycin represented by formula I is from 2 mL/g to 50 mL/g; and/or, the adding of anti-solvent is dropwise adding; the temperature of the dropwise adding of the anti-solvent is between 35 and 45° C.; and/or, the volume to mass ratio of the anti-solvent to the crude tulathromycin represented by formula I is from 2 mL/g to 60 mL/g.

20. The method according to claim 18, wherein when the anti-solvent is a mixed solvent of water and acetone, the volume ratio of water to acetone is from 0.5:1 to 3:1; when adding the anti-solvent, the adding is performed until the solution A containing tulathromycin represented by formula I turns turbid, the resulting mixture is stirred and crystalline grain culturing is carried out for 10 to 30 minutes, and the remaining anti-solvent is added; the temperature of the crystallization is between 0 and 45° C.; the duration of the crystallization is from 1 to 6 hours; the crystallization comprises an early stage of crystallization and a late stage of crystallization, wherein, the early stage of crystallization is carried out at a temperature between 35 and 45° C. for 0.5 to 3 hours, and the late stage of crystallization is carried out at a temperature between 0 and 35° C. for 0.5 to 3 hours.

* * * * *